US008663976B2

(12) United States Patent
Chung et al.

(10) Patent No.: US 8,663,976 B2
(45) Date of Patent: Mar. 4, 2014

(54) POLYMERASE CHAIN REACTION APPARATUS

(75) Inventors: Won-seok Chung, Suwon-si (KR); Kak Namkoong, Seoul (KR); Joon-ho Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 323 days.

(21) Appl. No.: 13/039,630

(22) Filed: Mar. 3, 2011

(65) Prior Publication Data

US 2012/0052531 A1 Mar. 1, 2012

(30) Foreign Application Priority Data

Aug. 30, 2010 (KR) ........................ 10-2010-0084184

(51) Int. Cl.
*C12M 1/34* (2006.01)
*C12M 3/00* (2006.01)

(52) U.S. Cl.
USPC .................. 435/287.2; 435/283.1; 435/287.1; 435/303.1

(58) Field of Classification Search
USPC .............. 435/287.2, 91.2, 303.1, 91.7, 283.1, 435/287.1; 422/500, 502, 503, 509, 525, 422/551, 560, 561, 563, 566, 567
See application file for complete search history.

(56) References Cited

U.S. PATENT DOCUMENTS

| | | | | |
|---|---|---|---|---|
| 4,865,986 | A | 9/1989 | Coy et al. | |
| 6,730,883 | B2 * | 5/2004 | Brown et al. | 219/428 |
| 2002/0072112 | A1 * | 6/2002 | Atwood et al. | 435/303.1 |
| 2007/0265439 | A1 | 11/2007 | Gumbrecht et al. | |
| 2009/0324451 | A1 * | 12/2009 | Yin et al. | 422/102 |

FOREIGN PATENT DOCUMENTS

| | | | |
|---|---|---|---|
| JP | 2007101347 | A | 4/2007 |
| KR | 1020010038297 | A | 5/2001 |
| KR | 1020060114525 | A | 11/2006 |
| KR | 1020060116983 | A | 11/2006 |
| KR | 1020100034986 | A | 4/2010 |
| WO | WO2008024080 | A1 * | 2/2008 |

* cited by examiner

*Primary Examiner* — Nathan Bowers
*Assistant Examiner* — Timothy Barlow
(74) *Attorney, Agent, or Firm* — Leydig, Voit & Mayer, Ltd.

(57) ABSTRACT

A polymerase chain reaction ("PCR") apparatus includes a PCR chip holder which accommodates and supports a PCR chip, a housing which supports ends of the PCR chip holder, a temperature control element which moves perpendicularly with respect to the PCR chip holder in a space between the housing and the PCR chip holder in the housing, and an elastic unit which elastically biases the temperature control element toward the PCR chip holder, between the temperature control element and the housing. The temperature control element includes a top surface which is selectively contacted to a bottom surface of the PCR chip.

16 Claims, 3 Drawing Sheets

POLYMERASE CHAIN REACTION APPARATUS

CROSS-REFERENCE TO RELATED APPLICATIONS

This application claims priority to Korean Patent Application No. 10-2010-0084184, filed on Aug. 30, 2010, and all the benefits accruing therefrom under 35 U.S.C. §119, the disclosure of which is incorporated herein in its entirety by reference.

BACKGROUND

1. Field

Provided are polymerase chain reaction ("PCR") apparatuses, and more particularly, a PCR apparatus including a unit for providing a close contact between a PCR chip and a thermal control element.

2. Description of the Related Art

Polymerase chain reaction ("PCR") technology for amplifying a certain region of deoxyribonucleic acid ("DNA") or ribonucleic acid ("RNA") in a reaction container is widely used not only in fields of genetic engineering and life science, but also in medical fields for diagnosing diseases. In order to efficiently perform PCR, it is essential to quickly and accurately adjust a temperature of a gene sample to be amplified, to a target temperature.

A PCR apparatus includes a thermal control element for heating and cooling a sample solution in a reaction chamber of a PCR chip in which PCR occurs. The PCR chip can be heated and cooled by the thermal control element in the form of conduction and, in order to efficiently transfer thermal energy between the PCR chip and the thermal control element, both of the PCR chip and the thermal control element should be closely contacted with each other.

When the PCR chip and the thermal control element are closely contacted with each other, the PCR chip or a contact part of the thermal control element may be damaged due to strong contact pressure. Specifically, if the PCR chip or the contact part of the thermal control element is composed of silicon which has high thermal diffusivity but is easily deformed to be broken, the PCR chip or the thermal control element may be damaged more severely. Accordingly, a unit for suitably adjusting contact pressure between the PCR chip and the thermal control element is required.

SUMMARY

Provided are polymerase chain reaction ("PCR") apparatuses for suitably adjusting contact pressure between a PCR chip and a thermal control element.

Embodiments will be set forth in part in the description which follows and, in part, will be apparent from the description, or may be learned by practice of the illustrated embodiments.

Provided is a PCR apparatus including a PCR chip holder which fixes and supports a PCR chip, a housing which supports both ends of the PCR chip holder, a temperature control element which selectively contacts a bottom surface of the PCR chip and moves perpendicularly to the bottom of the housing, and an elastic unit which elastically biases the temperature control element away from the bottom of the housing.

In an embodiment, the PCR chip holder may be attachable to and/or detachable from the housing.

In an embodiment, the PCR apparatus may further include a fixing unit in the housing, and the PCR chip holder is selectively fixed to the housing.

In an embodiment, the fixing unit may include a groove at each of facing sides of the housing, a elastic element held on a bottom of the groove of the housing, and a ball which is connected to the elastic element and selectively moves towards and away from a bottom of the groove of the housing by an elastic force of the elastic element. The PCR chip holder includes a concave groove at each of the opposing ends, and the ball of the fixing unit is in the concave groove when the opposing ends of the PCR chip holder are attached to the housing.

In an embodiment, the temperature control element may further include a printed circuit board ("PCB") facing the bottom of the housing and parallel to the contact part of the temperature control element, and a supporting member connected to both the contact part and the PCB. The supporting member maintains a predetermined interval between the contact part of the temperature control element and the PCB in the housing.

In an embodiment, the PCR apparatus may further include a stopper which overlaps the supporting member of the temperature control element, so as to limit a distance that the temperature control element moves away from the bottom of the housing, in the housing.

In an embodiment, the elastic unit may be an elastic spring.

In an embodiment, the contact part of the temperature control element may include silicon, and may include a heater, such as patterned line of metal, on a surface of the contact part of the temperature control element.

In an embodiment, the contact part of the temperature control element may be a Peltier element.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
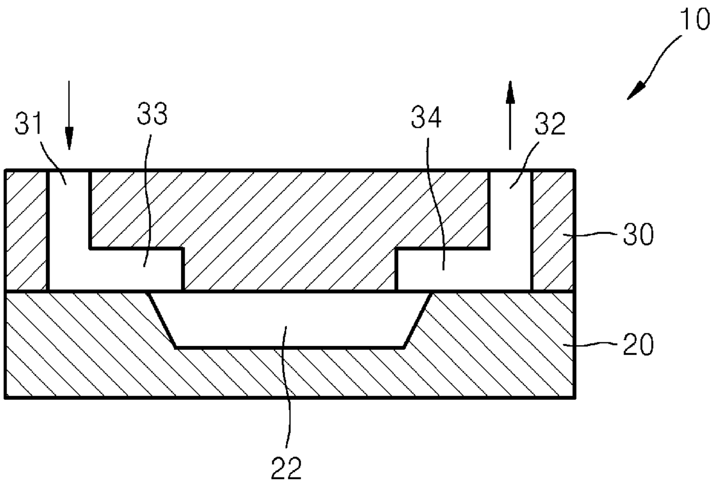
FIG. 1 is a cross-sectional view of an embodiment of a polymerase chain reaction ("PCR") chip according to the present invention.

Reference will now be made in detail to embodiments, examples of which are illustrated in the accompanying drawings. In the drawings, the thicknesses of layers and regions are exaggerated for clarity, and like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "lower," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the invention will be described in detail with reference to the accompanying drawings.

FIG. 1 is a cross-sectional view of an embodiment of a polymerase chain reaction ("PCR") chip 10 according to the present invention. Referring to FIG. 1, a lower substrate 20 may include a material having high thermal conductivity, such as silicon, and an upper substrate 30 may include a transparent material, such as glass or plastic. A chamber 22 in which PCR is to occur, may be in the lower substrate 20. The chamber 22 may extend from an upper surface or upper plane of the lower substrate 20, partially through a thickness of the lower substrate 20 and to an interior of the lower substrate 20.

The upper substrate 30 includes an inlet 31 and a first microchannel 33 through which a liquid is injected into the chamber 22, and a second microchannel 34 and an outlet 32 through which a reactant is discharged from the chamber 22 and to an outside of the PCR chip 10. In FIG. 1, only one chamber 22 is illustrated in the lower substrate 20, but the present invention is not limited to the one chamber 22. In an alternative embodiment, for example, a plurality of chambers 22 may be in one PCR chip 10. Where there is a plurality of chambers 22, the one PCR chip 10 may include a first microchannel, an inlet, a second microchannel and an outlet for each of the chambers.

The inlet 31 and the first microchannel 33 are in fluid communication with each other, and the second microchannel 34 and the outlet 32 are in fluid communication with each other. A continuous fluid channel may be respectively formed by the inlet 31 and the first microchannel 33, and by the second microchannel 34 and the outlet 32. The continuous fluid channel may extend from an upper surface or upper plane of the upper substrate 30, and completely through a thickness of the upper substrate 30, as illustrated in FIG. 1.

Figure 2:
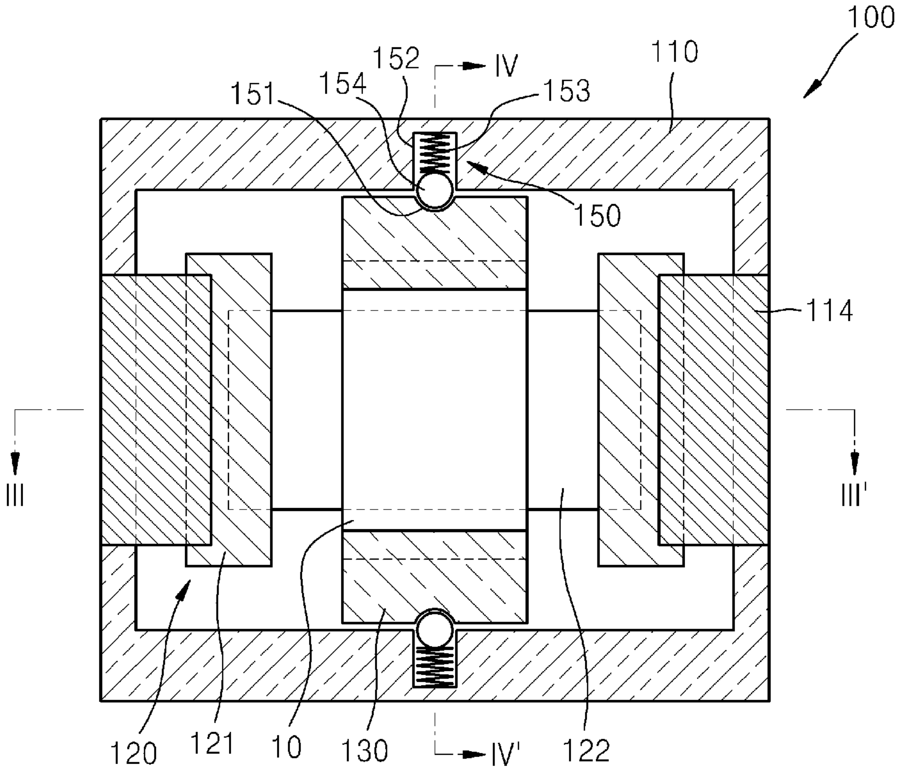
FIG. 2 is a plan view of an embodiment of a PCR apparatus according to the present invention.
Figure 3:
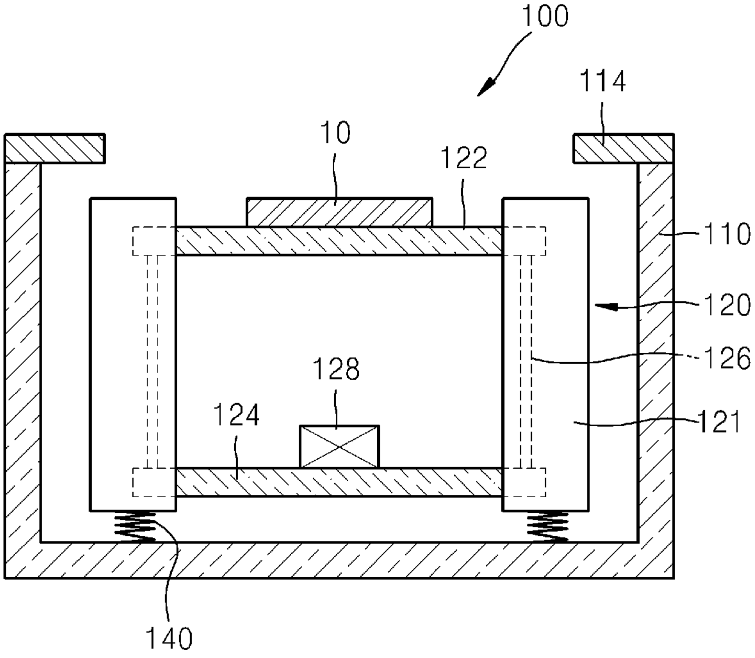
FIG. 3 is a cross-sectional view taken along line III-III' of FIG. 2.
Figure 4:
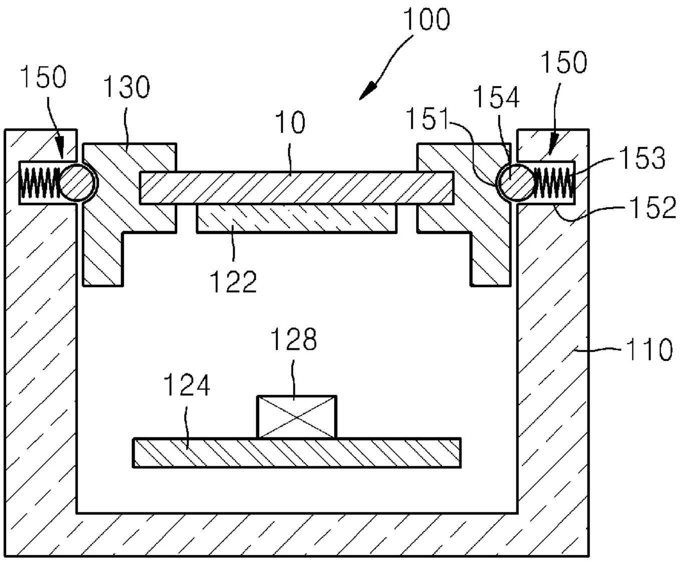
FIG. 4 is a cross-sectional view taken along line IV-IV' of FIG. 2.

FIG. 2 is a plan view of an embodiment of a PCR apparatus 100 according to the present invention, FIG. 3 is a cross-sectional view taken along line III-III' of FIG. 2, and FIG. 4 is a cross-sectional view taken along line IV-IV' of FIG. 2.

Referring to FIGS. 2 through 4, the PCR apparatus 100 includes a housing 110, a temperature control element 120 supported within the housing 110 through an elastic unit 140, and a PCR chip holder 130 whose two ends are supported by a side of the housing 110. The elastic unit 140 may be an elastic spring. The PCR apparatus 100 may include a single elastic unit 140, or a plurality of elastic units 140. The elastic unit 140 is between the temperature control element 120 and the bottom of the housing 110.

The housing 110 may include a bottom portion at the bottom of the housing 110, a pair of first sidewalls facing each other and extending from the bottom portion, and a pair of second sidewalls different from the first sidewalls, facing each other and extended from the bottom portion. A top of the housing 110 facing the bottom of the housing 110 may be substantially open, such that an inside of the housing 110 is accessible from an outside of the housing 110.

The PCR chip holder 130 fixes and supports the PCR chip 10 within the housing 110. The PCR chip holder 130 enables easy handling of the PCR chip 10, and stable contact between the PCR chip 10 and the temperature control element 120. The PCR chip holder 130 may be attached to and removed from the second sidewalls of the housing 110.

The temperature control element 120 may move up and down with respect to a bottom of the housing 110. In other words, a bottom of the temperature control element 120 is connected to and movable with respect to the bottom of the housing 110 through the elastic unit 140. The temperature control element 120 is elastically biased by the elastic unit 140 to be positioned away from the bottom of the housing 110, as illustrated in FIG. 3.

The housing 110 may include a plastic material. A stopper 114 for limiting a distance that the temperature control element 120 may travel in a direction away from the bottom of the housing 110 may be on a top portion of the housing 110. A portion of the stopper 114 overlaps a portion of the temperature control element 120, such that the temperature control element 120 is movable between the bottom of the housing 110 and a lower surface of the stopper 114.

The temperature control element 120 includes a supporting member 121, and a contact part 122 and a printed circuit board ("PCB") 124 that are connected to the supporting member 121. The contact part 122 and the PCB 124 are disposed in parallel to each other while being on the supporting member 121. The elastic unit 140 is connected to a bottom of the supporting member 121. The supporting member 121 may include two column elements, and each column element may respectively face the first sidewalls of the housing 110. As shown in FIG. 3, each of the two column elements of the supporting member 121 may be connected to each other by the PCB 124 and the contact part 122. The contact part 122 includes a silicon plate (not shown) having good thermal conductivity, and a heater, such as patterned line of metal (not shown) at a bottom of the silicon plate. The silicon plate directly contacts the PCR chip 10.

Wiring (not shown) for supplying power to the heater of the contact part 122 is on the PCB 124. The heater of the contact part 122 and the PCB 124 are electrically connected to each other by wiring 126 in the supporting member 121. A portion of the wiring 126 may be completely within each of the column elements, as indicated by the dotted outline shown in FIG. 3. Alternatively, an entire of the wiring 126 may be completely within only one of the column elements. The wiring 126 may include wiring for supplying a current to the heater of the contact part 122, and/or wiring connected to a temperature sensor (not shown) attached to the contact part 122 in order to measure temperature of the contact part 122. In embodiments, the temperature sensor may include, but is not limited to, at least one of a resistance temperature detector ("RTD"), a thermocouple, and a thermistor.

The PCR apparatus 100 may further include a fan 128. For convenience, the fan 128 is included in the housing 110, but the fan 128 may be disposed outside the housing 110. The fan 128 and the contact part 122 operate as a temperature control member of the PCR chip 10.

A fixing unit 150 is placed at the side of the housing 110 so as to fix the PCR chip holder 130 to a position at which the PCR chip 10 contacts the contact part 122, in the housing 110. An embodiment of the fixing unit 150 according to the invention is shown in FIGS. 2 and 4. The fixing unit 150 may include at least one concave groove 151 recessed into each of opposing ends of the PCR chip holder 130, a groove 152 in the housing 110 and a ball spring mechanism which protrudes into the groove 152 in the housing 110, to fix a position of the PCR chip holder 130 with respect to the housing 110. The groove 152 is disposed recessed into both of opposing sides of the housing 110, and may be aligned with the concave groove 151 of the PCR chip holder 130. The ball spring mechanism includes a spring 153 including a first end attached on a bottom of the groove 152 at a first side wall of the housing 110, and a ball 154 connected to a second end of the spring 153 opposing the first end. A first area of the ball 154 is connected to the second end of the spring 153, and a second area of the ball 154 opposing the first area, is in and connected to the concave groove 151 in the PCR chip holder 130. The PCR chip holder 130 may be fixed to the sidewall of the housing 110, by the ball spring mechanism.

Figure 5:
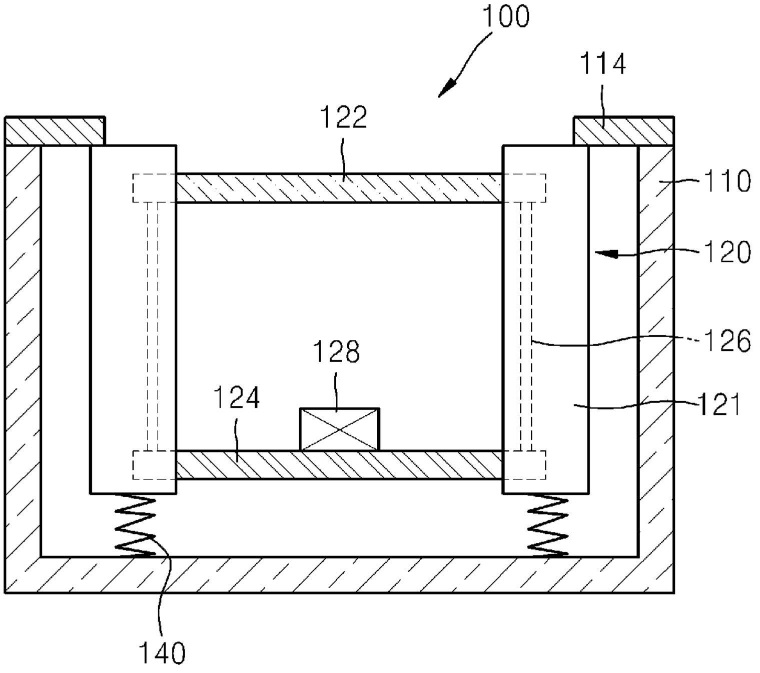
FIG. 5 is a diagram for describing operation of the PCR apparatus according to the present invention.

FIG. 5 is a diagram for describing operations of an embodiment of a PCR apparatus according to the present invention. Operations of the PCR apparatus 100 will now be described with reference to FIGS. 1 through 5.

FIG. 5 shows a state where the PCR chip holder 130 is not installed in the PCR apparatus 100. The temperature control element 120 is elastically biased upward in a direction away from the bottom of the housing 110 by the elastic unit 140. A vertical position of the temperature control element 120 is limited by the stopper 114, as shown by the supporting member 121 in contact with the lower surface of the stopper 114.

From the state in FIG. 5, FIGS. 3 and 4 show the operation of fixing the PCR chip holder 130 to the housing 110. The PCR chip holder 130 including the PCR chip 10 is initially placed between two first opposing sidewalls of the housing 110 on the contact part 122, in such a way that the concave groove 151 of the PCR chip holder 130 including the PCR chip 10 is placed at a location along two second opposing sidewalls different from the first opposing sidewalls and corresponding to the ball spring mechanism of the housing 110.

Then, the PCR chip holder 130 is pushed downward towards the bottom of the housing 110. With the concave groove 151 of the PCR chip holder 151 aligned with the ball spring mechanism along the two second opposing walls, when the PCR chip holder 130 is moved downward, the ball 154 enters the concave groove 151. When the concave groove 151 of the PCR chip holder 151 aligns with the groove 152 of the housing 110, the ball spring mechanism is fully released between the concave groove 151 and the groove 152, as the ball 154 contacts portions of the concave groove 151. Accordingly, the position of the PCR chip holder 130 is fixed relative to the housing 110 by the fixing unit 150. When the position of the PCR chip holder 130 is fixed relative to the housing 110 by the fixing unit 150, a lower surface of the PCR chip 10 on the PCR chip holder 130, contacts an upper surface of the contact part 122, as shown n FIG. 4.

Since an elastic force is applied to the temperature control element 120 in the direction away from the bottom of the housing by the elastic unit 140, and since the position of the PCR chip holder 130 is fixed by the fixing unit 150, the contact part 122 of the temperature control element 120 contacts the lower substrate 20 of the PCR chip 10 by the elastic force from the elastic unit 140.

Additionally, since the elastic unit 140 biases the temperature control member 120 in a direction away from the bottom portion of the housing 110, the lower surface of the PCR chip 10 contacts the upper surface of the contact part 122 solely by attaching and fixing the PCR chip holder 130 to the housing 110.

When the contact part 122 is in contact with the PCR chip 10, the contact part 122 is heated by supplying a current to the heater through the wiring 126. The temperature of the contact part 122 of the temperature control element 120 is maintained at a desired temperature by measuring the temperature of the contact part 122 through the wiring 126, and controlling the temperature of the contact part 122.

According to the PCR apparatus 100, when the PCR chip 10 and the contact part 122 closely contact each other, thermal energy transfers more rapidly between the contact part 122 and the PCR chip 10. Also, since the contact part 122 directly contacts the PCR chip 10 with predetermined pressure based on a predetermined elastic force from the elastic unit 140, damage to the PCR chip 10 and the contact part 122 are reduced or effectively prevented, even when the PCR chip 10 and the contact part 122 include a fragile material such as silicon.

In releasing the ball spring mechanism of the housing 110, such as by moving the ball 154 towards the bottom of the groove 152, the PCR chip holder 130 may be moved upward and away from the bottom of the housing 110, and may be removed from the PCR apparatus 100, thereby returning the PCR apparatus 100 to the state shown in FIG. 5. When the PCR chip holder 130 is removed from the PCR apparatus 100, a new PCR chip 10 may be mounted onto the PCR chip holder 130, and the PCR chip holder including the new PCR chip 10 may be reinserted into the PCR apparatus 100 as shown in FIGS. 3 and 4 discussed above. That is, the PCR chip holder 130 is removably disposed (e.g., both attachable to and detachable from the housing 110) with respect to the PCR apparatus 100.

Figure 6:
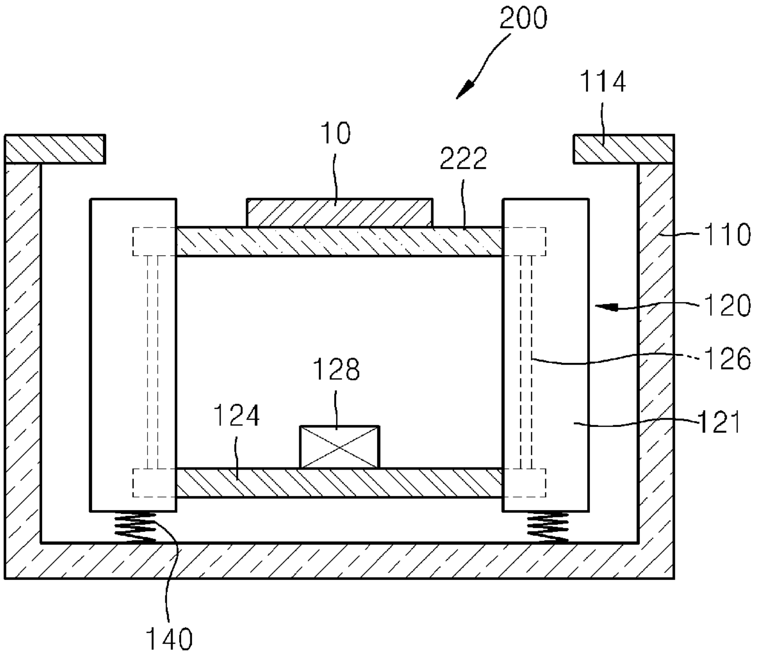
FIG. 6 is a cross-sectional view of another embodiment a PCR apparatus according to the present invention.

FIG. 6 is a cross-sectional view of another embodiment of PCR apparatus according to the present invention. Like reference numerals denote like elements in drawings, and thus details thereof are not repeated.

Referring to FIG. 6, a PCR apparatus 200 includes a Peltier element 222 instead of the contact part 122 of the PCR apparatus 100 in FIGS. 2-5. In the Peltier element 222, a plurality of pairs of p-columns and n-columns are arranged in series between two plates, and a direct current ("DC") voltage is applied to lead electrodes at ends of the plurality of pairs of p-columns and n-columns. A voltage may be applied to the lead electrodes through the wiring 126 in the supporting members 121 of the temperature control element 120. The plate of the Peltier element 222 contacting the PCR chip 10 heats up or cools down the PCR chip 10 based on the supplied voltage.

In an embodiment, the fan 128 and the Peltier element 222 may be attached to each other, while disposing a heat sink (not shown) therebetween. The Peltier element 222 and the fan 128 together operate as a temperature control member. Since the Peltier element 222 is well known to one ordinarily skilled in the art, detailed descriptions thereof are omitted.

An embodiment of the present invention also provides a method of controlling a temperature of a sample solution in a PCR chip, with reference to the PCR apparatus 100 in FIGS. 2-5. The method may also be applied to the PCR apparatus 200 in FIG. 6.

The method includes mounting the PCR chip 10 to the PCR chip holder 130, attaching the PCR chip holder 130 to both of facing sidewalls of the housing 100 of the PCR apparatus 100, contacting the temperature control element 120 in the housing of the PCR apparatus 100 to a lower surface of the PCR chip 10, and adjusting the temperature of the temperature control element 120, such that the temperature of the sample solution in the PCR chip 10 is controlled. To contact the temperature control element 120 to the lower surface of the PCR chip 10, the temperature control element 120 is biased in a first direction towards the PCR chip holder 130, while the PCR reaction chip holder 130 is simultaneously moved in a second direction opposite to the first direction during the attaching of the PCR chip holder 130 to the housing 110.

It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A polymerase chain reaction apparatus comprising:

a polymerase chain reaction chip holder to which a polymerase chain reaction chip is mounted;

a housing to which opposing ends of the polymerase chain reaction chip holder are attached;

an elastic unit on the bottom of a housing; and a temperature control element within the housing, wherein the temperature control element moves perpendicularly with respect to the bottom of the housing, and comprises a contact part which contacts a lower surface of the polymerase chain reaction chip, and distinct supporting members connected to the elastic unit and extending perpendicularly upward from the bottom of the housing and wherein opposing ends of the contact part are held by the supporting members at an end of the supporting members opposite where the supporting members connect to the elastic unit; and wherein the elastic unit elastically biases the temperature control element away from the bottom of the housing.

2. The polymerase chain reaction apparatus of claim 1, wherein the polymerase chain reaction chip holder is attachable to and detachable from the housing.

3. The polymerase chain reaction apparatus of claim 1, further comprising a fixing unit in the housing, wherein the PCR chip holder is attached to and detached from the housing by the fixing unit.

4. The polymerase chain reaction apparatus of claim 3, wherein the fixing unit comprises:

a groove at each of facing inner surfaces of the housing;

an elastic element on a bottom of the groove; and a ball connected to the elastic element, wherein the ball moves towards and away from the bottom of the groove by an elastic force of the elastic element, and the polymerase chain reaction chip holder comprises a concave groove at each of the opposing ends, and the ball of the fixing unit is in the concave groove when the opposing ends of the polymerase chain reaction chip holder are attached to the housing.

5. The polymerase chain reaction apparatus of claim 1, wherein the temperature control element further comprises:

a printed circuit board facing the bottom of the housing and parallel to the contact part of the temperature control element; and wherein the supporting members are connected to both the contact part and the printed circuit board so as to maintain a predetermined interval between the contact part and the printed circuit board.

6. The polymerase chain reaction apparatus of claim 5, further comprising a stopper which overlaps the supporting members of the temperature control element when viewed from a plan view, wherein the stopper limits a distance that the temperature control element moves away from the bottom of the housing when the stopper directly contacts the supporting members.

7. The polymerase chain reaction apparatus of claim 1, wherein the elastic unit is an elastic spring.

8. The polymerase chain reaction apparatus of claim 1, wherein the contact part of the temperature control element includes silicon, and comprises a heater on a surface of the contact part.

9. The polymerase chain reaction apparatus of claim 1, wherein the contact part of the temperature control element is a Peltier element.

10. The polymerase chain reaction apparatus of claim 6, wherein the housing has first sidewalls facing each other and extending perpendicularly with respect to the bottom of the housing, second sidewalls different from the first sidewalls, facing each other and extending perpendicularly with respect to the bottom portion, the stopper is disposed on the first sidewalls, and the polymerase chain reaction chip holder is selectively disposed on a top portion of the second sidewalls.

11. A polymerase chain reaction apparatus comprising:

a housing including:

a bottom portion, first sidewalls facing each other and extending perpendicularly with respect to the bottom portion; and second sidewalls different from the first sidewalls, facing each other and extending perpendicularly with respect to the bottom portion;

an elastic unit between the bottom portion of the housing and a temperature control member, wherein the elastic unit biases the temperature control member in a direction away from the bottom portion;

the temperature control member including:

distinct supporting members connected to the elastic unit and extending parallel with respect to the first sidewalls of the housing and respectively facing the first sidewalls of the housing, and extending perpendicularly upward from the bottom of the housing; and a contact part including opposing ends, wherein the opposing ends are held by the supporting members at an end of the supporting members opposite where the supporting members connect to the elastic unit;

a polymerase chain reaction chip holder to which a polymerase chain reaction chip is mounted, wherein the polymerase chain reaction chip holder is removably disposed with the second sidewalls of the housing; and wherein when the polymerase chain reaction chip holder is attached to the second sidewalls of the housing, the contact part of the temperature control member contacts a lower surface of the polymerase chain reaction chip mounted on the polymerase chain reaction chip holder.

12. The polymerase chain reaction apparatus of claim 11, further comprising a fixing unit comprising:

a first groove at each of inner surfaces of the second sidewalls of the housing;

an elastic element on a bottom of the first groove; and a ball connected to the elastic element, wherein the ball moves towards and away from the bottom of the first groove by an elastic force of the elastic element, and the polymerase chain reaction chip holder comprises a second groove at each of opposing ends of the polymerase chain reaction chip holder, and the ball of the fixing unit is in the second groove when second groove is aligned with the first groove and the polymerase chain reaction chip holder is attached to the second sidewalls of the housing.

13. The polymerase chain reaction apparatus of claim 11, wherein the temperature control member further includes:

a printed circuit board facing the bottom portion of the housing, and extended parallel to the contact part of the temperature control member; and wherein the supporting members are connected to both the contact part and the printed circuit board, and wherein the supporting members maintain a predetermined interval between the contact part and the printed circuit board.

14. The polymerase chain reaction apparatus of claim 13, wherein the housing further includes a top portion facing the bottom portion, the top portion overlapping the supporting members of the temperature control member, and when the polymerase chain reaction chip holder is not attached to the second sidewalls of the housing, the supporting members of the temperature control member contact the top portion of the housing.

15. The polymerase chain reaction apparatus of claim 12, further comprising a stopper which overlaps the supporting members of the temperature control member when viewed from a plan view, wherein the stopper limits a distance that the temperature control member moves away from the bottom of the housing when the stopper directly contacts the supporting members.

16. The polymerase chain reaction apparatus of claim 15, wherein the stopper is disposed on the first sidewalls.

* * * * *